__US012035894B2__

United States Patent
Pang et al.

(10) Patent No.: US 12,035,894 B2
(45) Date of Patent: Jul. 16, 2024

(54) SYSTEMS AND METHODS FOR MEDICAL IMAGING ILLUMINATION

(71) Applicant: Stryker Corporation, Kalamazoo, MI (US)

(72) Inventors: Chien Mien Pang, San Jose, CA (US); Eric Charles Huynh, San Ramon, CA (US); Ajay Ramesh, Pleasanton, CA (US); William Huei Liang Chang, Milpitas, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/558,561

(22) Filed: Dec. 21, 2021

(65) Prior Publication Data

US 2022/0192476 A1    Jun. 23, 2022

Related U.S. Application Data

(60) Provisional application No. 63/129,476, filed on Dec. 22, 2020.

(51) Int. Cl.
*A61B 1/06* (2006.01)
*A61B 1/005* (2006.01)
(Continued)

(52) U.S. Cl.
CPC .......... *A61B 1/0661* (2013.01); *A61B 1/0052* (2013.01); *A61B 1/042* (2013.01); *H04N 23/74* (2023.01)

(58) Field of Classification Search
None
See application file for complete search history.

(56) References Cited

U.S. PATENT DOCUMENTS 4,625,236 A * 11/1986 Fujimori ................ H04N 23/74
                                                             348/69
6,485,414 B1* 11/2002 Neuberger ............. A61B 1/063
                                                             600/178

(Continued)

FOREIGN PATENT DOCUMENTS

| EP | 2465433 A1 | 6/2012 |
|---|---|---|
| WO | 2010/016859 A1 | 2/2010 |
| WO | 2020/035929 A1 | 2/2020 |

OTHER PUBLICATIONS

International Preliminary Report on Patentability dated Jun. 13, 2023, directed to International Application No. PCT/US2021/064689; 7 pages.

(Continued)

*Primary Examiner* — John P Leubecker
*Assistant Examiner* — Jae Woo
(74) *Attorney, Agent, or Firm* — Morrison & Foerster LLP

(57) ABSTRACT

A light source for illuminating a target for medical imaging include a first light emitter package comprising a first light emitter that emits light having a first wavelength band and a second light emitter that emits light having a second wavelength band that is different than the first wavelength band; and a controller for operating the light source in a first mode in which the first light emitter is activated and the second light emitter is deactivated and a second mode in which the first light emitter is deactivated and the second light emitter is activated.

26 Claims, 8 Drawing Sheets

(51) Int. Cl.
  *A61B 1/04*     (2006.01)
  *H04N 23/74*    (2023.01)

(56) References Cited

U.S. PATENT DOCUMENTS

| | | | | |
|---|---|---|---|---|
| 6,682,207 | B2* | 1/2004 | Weber | H01S 5/423 |
| | | | | 362/230 |
| 7,347,817 | B2 | 3/2008 | Glukhovsky et al. | |
| 7,488,101 | B2 | 2/2009 | Brukilacchio | |
| 7,521,667 | B2* | 4/2009 | Rains, Jr. | G09F 13/22 |
| | | | | 362/257 |
| 8,408,772 | B2 | 4/2013 | Li | |
| 9,547,165 | B2* | 1/2017 | Yang | A61B 1/043 |
| 10,993,607 | B2* | 5/2021 | Omori | A61B 1/043 |
| 2003/0048239 | A1* | 3/2003 | Cok | H04N 1/484 |
| | | | | 345/55 |
| 2005/0135095 | A1* | 6/2005 | Geissler | G03B 21/2066 |
| | | | | 362/231 |
| 2005/0147135 | A1* | 7/2005 | Kurtz | H01S 5/423 |
| | | | | 348/E9.027 |
| 2005/0152146 | A1* | 7/2005 | Owen | H05B 47/10 |
| | | | | 362/294 |
| 2005/0174473 | A1* | 8/2005 | Morgan | H05B 45/355 |
| | | | | 348/370 |
| 2007/0278934 | A1* | 12/2007 | Van De Ven | G02F 1/133617 |
| | | | | 313/503 |
| 2009/0021739 | A1* | 1/2009 | Tsujita | H04N 25/134 |
| | | | | 356/407 |
| 2009/0306478 | A1* | 12/2009 | Mizuyoshi | A61B 1/0655 |
| | | | | 600/178 |
| 2011/0050125 | A1* | 3/2011 | Medendorp, Jr. | H05B 47/10 |
| | | | | 362/231 |
| 2011/0184243 | A1* | 7/2011 | Wright | A61B 1/0607 |
| | | | | 600/180 |
| 2012/0257030 | A1* | 10/2012 | Lim | A61B 1/0638 |
| | | | | 348/70 |
| 2012/0307512 | A1* | 12/2012 | Cogger | G02B 21/06 |
| | | | | 362/231 |
| 2015/0216460 | A1 | 8/2015 | Shigeta | |
| 2017/0035280 | A1* | 2/2017 | Yang | A61B 1/0646 |
| 2018/0317754 | A1 | 11/2018 | Yamamoto | |
| 2020/0170492 | A1* | 6/2020 | Kuramoto | A61B 5/489 |
| 2020/0337540 | A1 | 10/2020 | Takekoshi | |
| 2021/0011274 | A1* | 1/2021 | Otterstrom | A61B 1/0646 |
| 2021/0307613 | A1* | 10/2021 | Fengler | A61B 1/0684 |

OTHER PUBLICATIONS

International Search Report and Written Opinion mailed Mar. 14, 2022, directed to International Application No. PCT/US2021/064689; 12 pages.

Luminus Devices, Inc. (May 2018). "SBM-40-SC Product Datasheet" PDS-002984 Rev 02; 17 pages.

* cited by examiner

SYSTEMS AND METHODS FOR MEDICAL IMAGING ILLUMINATION

CROSS-REFERENCE TO RELATED APPLICATIONS

This application claims the benefit of U.S. Provisional Application No. 63/129,476, filed Dec. 22, 2020, the entire contents of which are hereby incorporated by reference herein.

FIELD

The present disclosure relates generally to medical imaging, and more particularly to illumination for medical imaging.

BACKGROUND

Advances in modern endoscopic imaging have pushed the need for imaging modalities beyond white light imaging. Two imaging techniques that are increasingly important in the endoscopic imaging field are near-infrared fluorescence imaging and narrow band imaging. Near-infrared fluorescence imaging uses a near-infrared light source to excite various fluorescently labelled structures in the body. Narrow band imaging uses, for example, ultraviolet and green light sources to better visualize surface blood vessel structures in the tissue.

A light source configured for providing illumination for white light imaging, near-infrared fluorescence imaging, and narrow band imaging modalities may include at least five light channels: an ultraviolet light channel for narrow band imaging, a blue light channel for white light imaging and optionally narrow band imaging, a green light channel for white light imaging and narrow-band imaging, a red light channel for white light imaging, and a near-infrared light channel for near-infrared fluorescence imaging. Dichroic filters and other optical elements can be used to combine the light from the different channels into a single beam. Generally, the greater the number of light channels and accompanying dichroic filters the more costly the light source is to manufacture and larger the light source may be. Additionally, light output efficiency may be sacrificed due to losses through the additional dichroic filters.

SUMMARY

According to an aspect, a light source for medical imaging combines at least two light emitters that produce light having different wavelength bands in the same channel. The two light emitters can be incorporated into the same light emitter package. Thus, two different colors share the same space within the light source, which can reduce the size, cost, and complexity of the light source and improve light output efficiency relative to one in which the colors are provided by emitters in dedicated spaces within the light source. Optionally, colors that are not used simultaneously may be combined in the same package so that a heat sink configured for cooling the package can be sized or otherwise configured for dissipating heat from just one emitter (or group of same type emitters) at a time, which can also provide size, cost, and complexity benefits.

According to an aspect, a light source for illuminating a target for medical imaging includes a first light emitter package comprising a first light emitter that emits light having a first wavelength band and a second light emitter that emits light having a second wavelength band that is different than the first wavelength band; and a controller for operating the light source in a first mode in which the first light emitter is activated and the second light emitter is deactivated and a second mode in which the first light emitter is deactivated and the second light emitter is activated.

Optionally, the light source may include a second light emitter package comprising a third light emitter that emits light having a third wavelength band that is different than the first and second wavelength bands; and a first optical element for combining emissions from at least the first and second light emitter packages into a combined light beam. The controller can be configured so that, in the first light mode, the third light emitter is activated.

Optionally, the first light emitter package comprises a substrate and the first light emitter and the second light emitter are mounted directly to the substrate.

Optionally, the light source comprises a first heat sink for dissipating heat from the first light emitter package and a second heat sink for dissipating heat from the second light emitter package. The first light emitter may generate a first amount of heat when activated in the first mode, the second light emitter may generate a second amount of heat when activated in the second mode, and a sum of the first amount of heat and the second amount of heat may be greater than a heat dissipation capacity of the first heat sink.

Optionally, a second optical element is located in front of the first light emitter and the second light emitter for receiving light from the first light emitter and the second light emitter and directing the received light to the first optical element.

Optionally, the third light emitter is activated in the second mode.

Optionally, the light having the first wavelength band and the light having the third wavelength band include visible light and the light having the second wavelength band includes non-visible light. The non-visible light may include ultraviolet light. The non-visible light may include infrared light.

Optionally, the light source includes a third light emitter package that includes a fourth light emitter that emits light having a fourth wavelength band that is different than the first, second, and third wavelength bands. The controller can be configured to activate the fourth light emitter along with the first light emitter and the third light emitter in the first mode for generating white light.

Optionally, the controller is configured to control the first light emitter and the second light emitter so that the first light emitter and the second light emitter are not activated at the same time.

Optionally, the first light emitter package includes a plurality of first light emitters and a plurality of second light emitters.

Optionally, the first light emitters are mosaiced with the second light emitters.

Optionally, the light source is configured for endoscopic imaging.

According to an aspect, a method for illuminating a target for medical imaging includes: emitting light having a first wavelength band from a first light emitter of a first light emitter package while a second light emitter of the first light emitter package remains deactivated, the second light emitter configured to emit light having a second wavelength band that is different than the first wavelength band; and deactivating the first light emitter of the first light emitter package and activating the second light emitter of the first light emitter package to emit the light having the second wavelength band to illuminate the target with light that includes the second wavelength band and lacks the first wavelength band. It is noted that the method concerns the operating of the light source. There is no functional link between the method and effects produced by the light source on the body.

Optionally, the method further includes, while emitting the light having the first wavelength band from the first light emitter, emitting light having a third wavelength band that is different than the first and second wavelength bands from a third light emitter of a second light emitter package, and combining the light from the first and second light emitter packages into a combined light, and illuminating the target with the combined light;

Optionally, the method further includes, while emitting the light having the first wavelength band and the light having the third wavelength band, generating a temporal sequence of images of the target.

Optionally, the method further includes generating a temporal sequence of images while alternatingly activating and deactivating the first and second light emitters. Optionally, the method includes generating a temporal sequence of images while alternatingly in a first mode the first light emitters are on and the second light emitters are off, and in a second mode the first light emitters are off and the second light emitters are on.

Optionally, the method further includes, while emitting the light having the first and third wavelength bands, emitting light having a fourth wavelength band that is different from the first and third wavelength bands to generate white light.

Optionally, the first light emitter package includes a substrate and the first light emitter and the second light emitter are mounted directly to the substrate.

Optionally, a first heat sink dissipates heat from the first light emitter package and a second heat sink, that can be different than the first heat sink, dissipates heat from the second light emitter package.

Optionally, the third light emitter remains activated while the first light emitter is deactivated and the second light emitter is activated.

Optionally, the light having the first wavelength band and the light having the third wavelength band include visible light and the light having the second wavelength band includes non-visible light. The non-visible light may include ultraviolet light. The non-visible light may include infrared light.

Optionally, the method includes illuminating the target with an endoscope.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The invention will now be described, by way of example only, with reference to the accompanying drawings, in which.

DETAILED DESCRIPTION

Figure 1A:
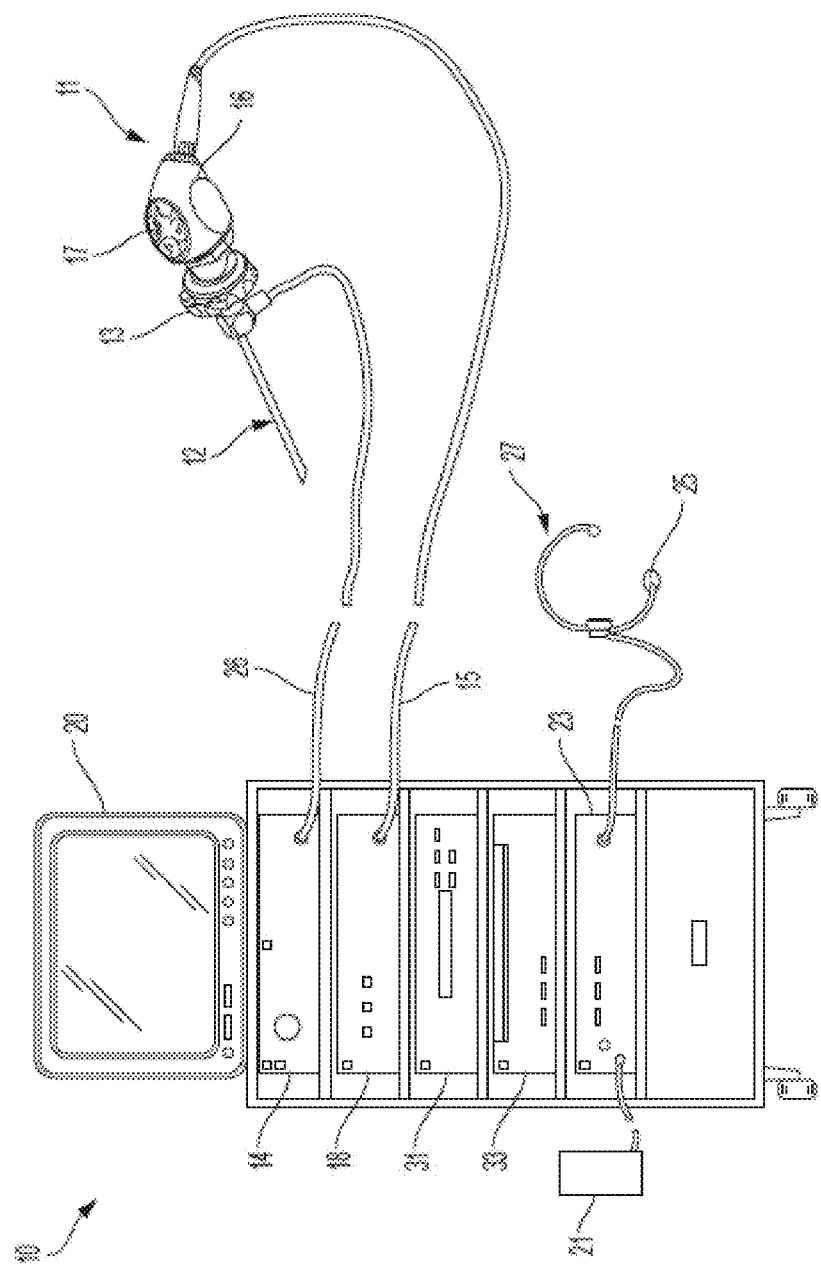
FIG. 1A is an illustration of an exemplary endoscopic camera system.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

According to various aspects, systems and methods for providing illumination for medical imaging include combining multiple colors, or wavelength bands, in the same channel of a light source. An illumination system can include at least two different color light emitters that are integrated in the same light emitter package and can be driven independently of one another. The package can be thermally coupled to a single heat sink configured for cooling the package. One or more optical components can be positioned downstream of the emitters such that the emitters share the same optical components. Thus, two different colors can be provided in the same space, which can reduce the size, cost, and complexity of the light source and improve light output efficiency relative to a light source in which the colors are provided in separate channels. The different color emitters of the same package are independently driven and controlled. A controller can be configured to control the emitters in a first mode in which the first emitter is activated and the second emitter is deactivated and a second mode in which the first emitter is deactivated and the second emitter is activated.

The illumination system can include one or more additional channels that provide light simultaneously with the first and/or second emitter of the first channel. For example, the controller can be configured to activate the first emitter of the first channel and an emitter of a second channel that generates a third wavelength band that is a different wavelength band from the first and second wavelength bands so that the illumination system provides light having at least the first and third wavelengths but not the second. When the first light emitter is deactivated and the second activated, the emitter of the second channel can remain activated or can be deactivated.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

As used herein, the term "color" refers to visible and non-visible wavelength bands.

FIG. 1A shows an example of an endoscopic imaging system 10, which includes an endoscopic camera system 11 which may be utilized in endoscopic procedures. The endoscopic camera system 11 incorporates an endoscope or scope 12 which is coupled to a camera head 16 by a coupler 13 located at the distal end of the camera head 16. Light is provided to the scope 12 by a light source 14, which can be configured according to the principles described herein. The light source 14 can provide light to the scope 12 via a light guide 26, such as a fiber optic cable. The camera head 16 is connected to a camera control unit (CCU) 18 by an electrical cable 15. The CCU 18 is connected to, and communicates with, the light source 14. Operation of the camera 16 is controlled, in part, by the CCU 18. The cable 15 conveys video image and/or still image data from the camera head 16 to the CCU 18 and may convey various control signals bi-directionally between the camera head 16 and the CCU 18.

A control or switch arrangement 17 may be provided on the camera head 16 for allowing a user to manually control various functions of the system 10, which may include switch from one imaging mode to another, which in some examples, may cause the light source 14 to switch illumination modes, as discussed further below. Voice commands may be input into a microphone 25 mounted on a headset 27 worn by the practitioner and coupled to the voice-control unit 23. A hand-held control device 29, such as a tablet with a touch screen user interface or a PDA, may be coupled to the voice control unit 23 as a further control interface. In the illustrated example, a recorder 31 and a printer 33 are also coupled to the CCU 18. Additional devices, such as an image capture and archiving device, may be included in the system 10 and coupled to the CCU 18. Video image data acquired by the camera head 16 and processed by the CCU 18 is converted to images, which can be displayed on a monitor 20, recorded by recorder 31, and/or used to generate static images, hard copies of which can be produced by the printer 33.

Figure 1B:
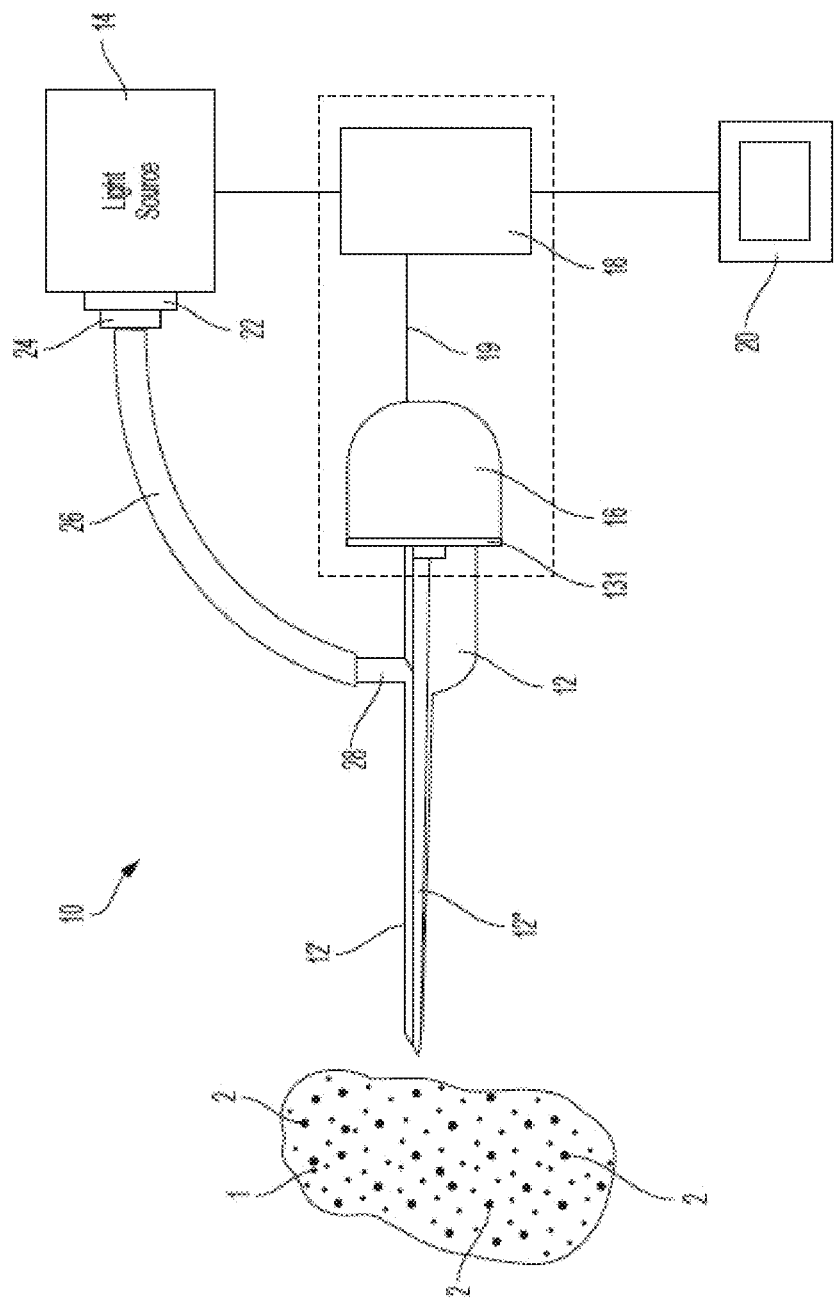
FIG. 1B is a diagram of a portion of the endoscopic camera system of FIG. 1A and a target object for imaging.

FIG. 1B shows an example of a portion of the endoscopic system 10 being used to illuminate and receive light from an object 1, such as tissue of a patient. The object 1 may include fluorescent markers 2, for example, as a result of the patient being administered a fluorescence imaging agent. The fluorescent markers 2 may be comprised of, for example, indocyanine green (ICG).

As discussed in more detail below, the light source 14 can generate one or more of visible illumination light (such as any combination of red, green, and blue light) for generating visible (e.g., white light) images of the target object 1, fluorescence excitation illumination light for exciting the fluorescent markers 2 (e.g., near-infrared fluorescence excitation illumination light for exciting near-infrared fluorescent markers) in the target object 1 for generating fluorescence images, and ultraviolet light for fluorescence excitation light or for narrow-band imaging. Illumination light is transmitted to and through an optic lens system 22 which focuses light onto a light pipe 24. The light pipe 24 may create a homogeneous light, which is then transmitted to the fiber optic light guide 26. The light guide 26 may include multiple optic fibers and is connected to a light post 28, which is part of the endoscope 12. The endoscope 12 includes an illumination pathway 12' and an optical channel pathway 12".

The endoscope 12 may include a notch filter 131 that allows some or all (preferably, at least 80%) of fluorescence emission light (e.g., in a wavelength range of 830 nm to 870 nm) emitted by fluorescence markers 2 in the target object 1 to pass and that allows some or all (preferably, at least 80%) of visible light (e.g., in the wavelength range of 400 nm to 700 nm), such as visible illumination light reflected by the target object 1, to pass, but that blocks substantially all of the fluorescence excitation light (e.g., infrared light having a wavelength of 808 nm) that is used to excite fluorescence emission from the fluorescent marker 2 in the target object 1. The notch filter 131 may have an optical density of OD5 or higher. In some examples, the notch filter 131 can be located in the coupler 13.

Figure 2:
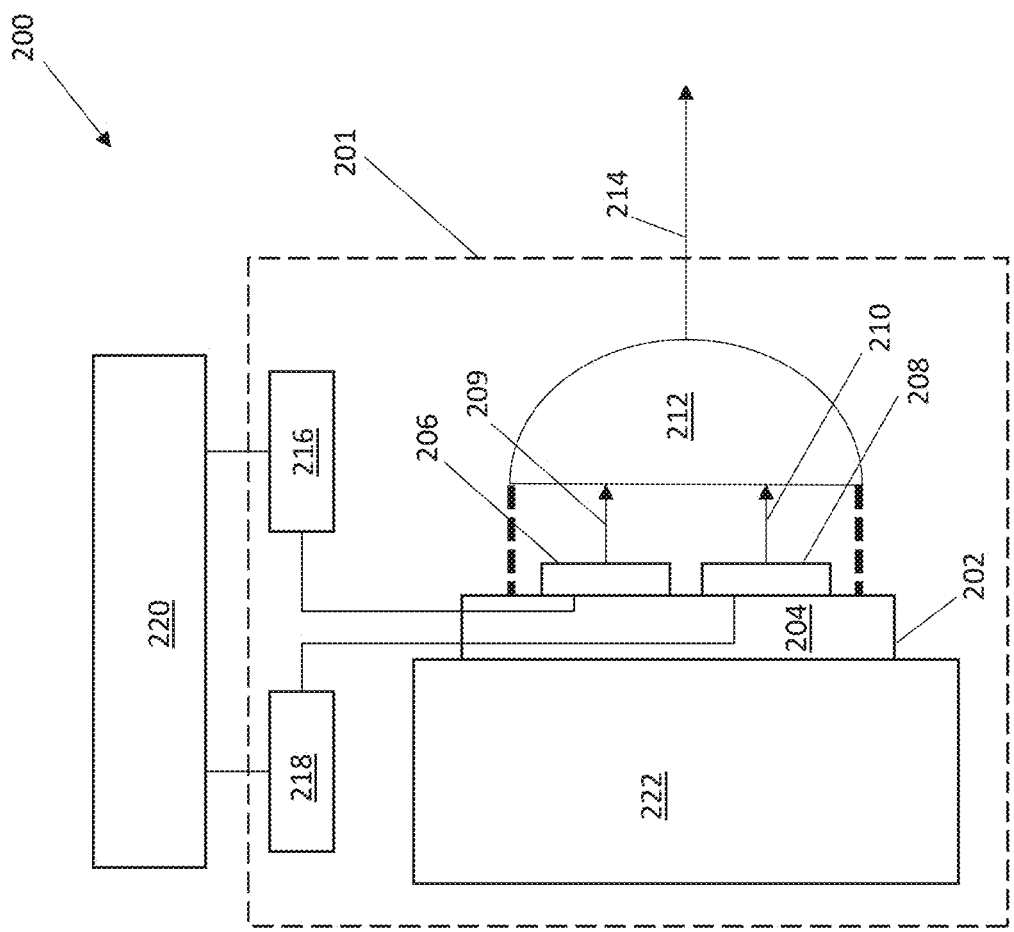
FIG. 2 is a block diagram of an exemplary illumination system configured to provide illumination light for medical imaging.

FIG. 2 is a block diagram of an exemplary illumination system 200 configured to provide illumination light for medical imaging. Illumination system 200 can be used for light source 14 of system 10 of FIG. 1A,B. System 200 incorporates at least two different colors into the same illumination module, which can reduce cost, provide a more compact illumination system, and/or improve optical efficiency relative to a conventional system in which the two colors are provided in their own modules. System 200 comprises at least one multi-color illuminator module 201 that includes a light emitter package 202 configured to emit at least two different wavelength bands, a heat sink 222 for dissipating heat generated by the light emitter package 202, and at least one optical component 212 positioned in front of the light emitter package 202 for receiving light from the light emitter package 202 and directing the light along a light path 214.

The light emitter package 202 can include a substrate 204, a first light emitter 206 mounted on the substrate 204 and a second light emitter 208 mounted on the substrate 204. The first light emitter 206 is configured to output first light 209 having a first wavelength band and the second light emitter 208 is configured to output second light 210 having a second wavelength band that is different than the first wavelength band. Optionally, the first and second light emitters 206, 208 are mounted directly to the substrate 204. In some examples, the light emitters 206, 208 are directly bonded to the substrate 204, such as using a thermally conductive bonding. In some examples, the substrate 204 is a printed circuit board (PCB), which may provide the electrical interconnection between the light emitters 206, 208 and their respective drivers 216, 218. The emitters 206, 208 can be electrically connected to electrical traces of the substrate via surface mount technology (SMT). In some examples, the light emitters 206, 208 are each semiconductor chips.

The substrate 204 can be mounted to a heat sink 222 that is configured to absorb and dissipate heat generated by the emitters 206, 208. This provides a cost and space savings over a conventional system in which the emitters 206, 208 are provided in their own dedicated modules since it requires just one heat sink instead of two. In some examples, the heat sink 222 is configured to dissipate heat from just one of the emitters 206, 208 at a time, taking advantage of the fact that the two emitters 206, 208 may not be active simultaneously. In other words, the heat sink 222 may be configured with a maximum heat dissipation rate that is above the maximum heat generation rate of one of the emitters 206, 208 but below the combined heat generation rate of the emitters 206, 208. Therefore, the heat sink 222 does not need to be twice as large to accommodate both emitters 206, 208. In other examples, the heat sink is configured for both emitters 206, 208 to be used simultaneously.

Each of the first and second light emitters 206, 208 is electrically independent from one another and driven by its own driver. The first light emitter 206 is driven by first driver 216 and second light emitter 208 is driven by second driver 218. The drivers 216, 218 independently drive the respective light emitter 206, 208 based on control commands from controller 220. In some examples, the controller 220 can control the drivers 216, 218 to provide at least two different illumination modes. In a first illumination mode, the first driver 216 is controlled to drive first light emitter 206 to emit the first light 208 and the second driver 218 is controlled so that the second light emitter 208 is off. The controller can switch to a second mode in which the second driver 218 is controlled to drive second light emitter 208 to emit the second light 210 and the first driver 216 is controlled so that the first light emitter 206 is off. The controller 220 may be configured to control the drivers 216, 218 to provide additional illumination modes, including providing light from both the first and second light emitters 206, 208 simultaneously. The controller 220 may be configured to control the drivers 216, 218 to control the intensity of light output from the respective emitters, such as by altering the current driving the emitters and/or controlling a pulsing of the emitters.

The at least one optical component 212 can be configured to receive the first light 209 from the first light emitter 206 and the second light 210 from the second light emitter 208 and direct it along a common light path 214, which may lead to a light output from the illumination system 200 either directly or via one or more additional optical components such as one or more mirrors, dichroics, lenses, etc. In some examples, the optical component 212 is directly mounted to the substrate 204. In other examples, the optical component 212 is not mounted to the substrate but, rather, is mounted via a separate mounting arrangement. In some examples, the optical component 212 is configured to decrease the angle of the paths of first and second light 209, 210.

Illumination system 200 can be configured to provide illumination light for at least two different imaging modalities and can be controlled to switch between two different illumination modes for the two different imaging modalities. For example, the first light emitter 206 may be configured to generate white light that can be used to illuminate an imaging field of view for a white light imaging modality and the second light emitter can be configured to generate fluorescence excitation light for exciting a fluorescence target in the imaging field of view for a fluorescence imaging modality. The controller 220 can be configured to switch from the first mode in which the first light emitter 206 is controlled to provide white light and the second light emitter 208 is off to the second mode in which the first light emitter 206 is off and the second light emitter 208 is controlled to provide fluorescence excitation light. In some examples, the first mode and/or the second mode are continuous for at least a period of multiple imaging frames. For example, an imaging system may be used in a white light only mode for a period of multiple imaging frames in which the illumination system 200 provides white light from the first light emitter 206 continuously and the second light emitter 208 remains deactivated for the multiple imaging frames. In some examples, the illumination system 200 may be switched to a fluorescence-only imaging mode in which the second light emitter 208 provides fluorescence excitation light continuously and the first light emitter 206 remains off for multiple imaging frames.

The first and second light emitters 206, 208 can include any suitable semiconductor light emitter, including one or more light emitting diodes (LED) and/or one or more laser diodes. In some examples, a first or second emitter includes a plurality of LEDs of the same type emitting the same wavelength band. In some examples, the light emitter package 202 includes multiple first light emitters 206 and/or multiple second light emitters 208. For example, the light emitter package 202 may have a 3×2 matrix, a 4×4 matrix, an 8×8 matrix, etc., of first and second light emitters. The first and second light emitters can be provided in separate sections of the package or can be mosaiced together. In some examples, the light emitter package 202 includes one or more additional light emitters generating light having one or more additional wavelength bands that are different than the first and second wavelength bands. For example, in some examples, a light emitter package 202 includes a red LED, a green LED, and a blue LED that are activated simultaneously in a first mode to produce white light for a white light imaging modality and also includes an LED configured to generate fluorescence excitation light in a second mode for a fluorescence illumination modality. As is well-known in the art, emitters can be configured for generating a desired wavelength band, such as by using different light emitter materials, different phosphor coatings, and/or using a filter layer. As such, various examples can include emitters that generate any desired wavelength band, including visible wavelength bands, such as red, green, and blue, and non-visible wavelength bands, such as one or more infrared bands and one or more ultraviolet bands. According to some examples, the wavelength bands of emitters of a multi-color channel are adjacent one another on the color spectrum relative to the colors of other emitters of the light source. According to some examples, the wavelength bands of the emitters of a multi-color channel are non-overlapping. According to some examples, the wavelength bands of the emitters of a multi-color channel are overlapping.

Figure 3A:
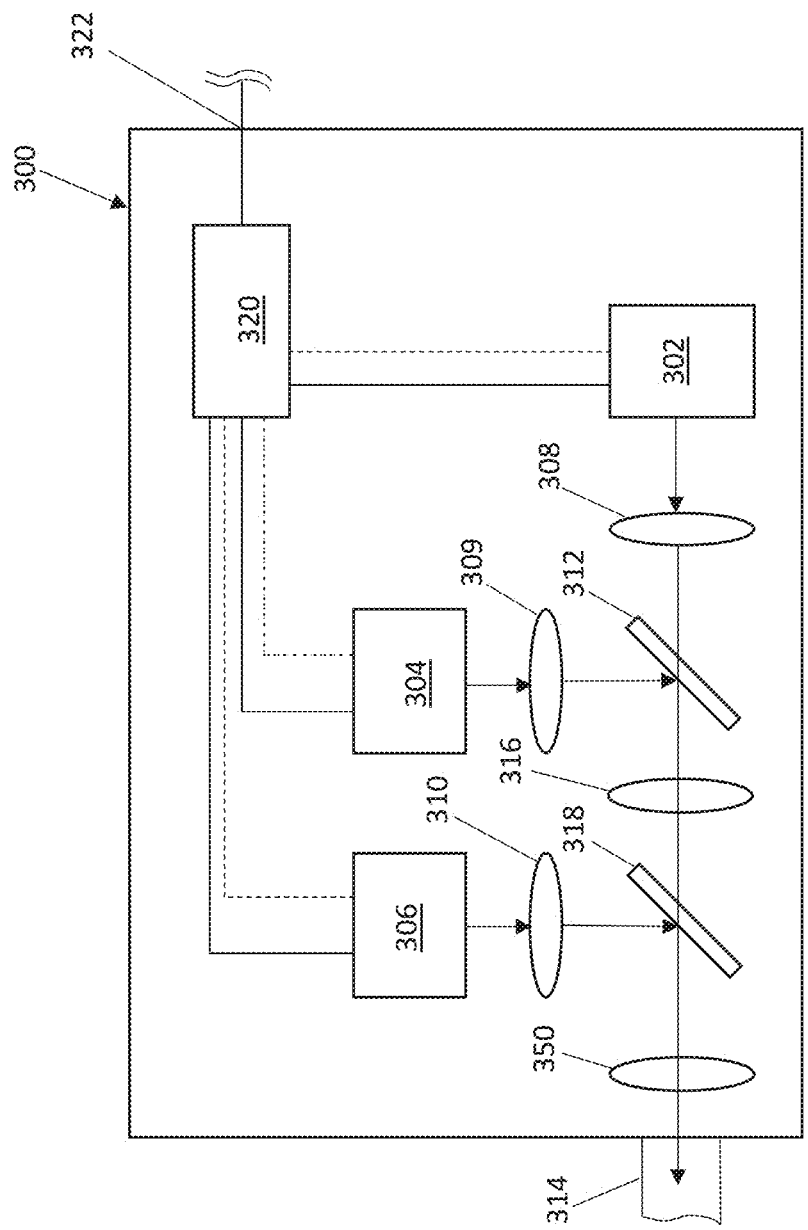
FIG. 3A is a block diagram of an exemplary medical imaging illumination system that can generate at least four different wavelength bands with three illuminator modules.

FIG. 3A is a block diagram of a medical imaging illumination system 300 that can generate at least four different wavelength bands with three illuminator modules. System 300 includes first illuminator module 302, second illuminator module 304, and third illuminator module 306. One or more of the illuminator modules 302, 304, 306 can be a multi-color illuminator module, such as multi-color illuminator module 201 of system 200, to provide at least two different wavelength bands from two different emitters of the same emitter package, as represented by the dashed lines in FIG. 3A. As such, one or more of the illuminator modules 302, 304, 306 may have an emitter package that has at least two illuminators mounted on a substrate and configured to generate light having at least two different wavelength bands, a single heat sink for the illuminator package, and a separate illuminator driver for each distinct type of illuminator. In some examples, one or more of the illuminator modules 302, 304, 306 may be configured as a single color illuminator module providing just a single wavelength band of light. In some examples, a single color illuminator module can be configured similarly to illuminator module 201 of system 200 except that the one or more emitters of the module are a single color. Thus, an illuminator module 302, 304, 306 configured as a single-color module can include one or more emitters mounted on a substrate that is thermally bonded to a heat sink, and an optical component can be mounted to the substrate in front of the one or more emitters. The single color module include a single emitter driver for driving the emitter(s) of the module.

In some examples, one or more first optical components 308 may be positioned downstream of the first illuminator module 302 for shaping the light from the first illuminator module 302 (which may include light that has passed through the one or more optical components of the illuminator module). Similarly, one or more second optical components 309 may be positioned downstream of the second illuminator module 304 and one or more third optical components 310 may be positioned downstream of the third illuminator module 306. A first dichroic filter 312 may be positioned downstream of the one or more second optical components 309 to reflect light from the second illuminator module 304 toward a light output 314 of the illumination system 300. The first dichroic filter 312 is configured to reflect light in the wavelength band(s) generated by the second illuminator 304 and to pass light in the wavelength band(s) generated by the first illuminator module 302. At least one fourth optical component 316 may be positioned downstream of the first dichroic filter 312 for shaping light reflected by and passed through the first dichroic filter 312. A second dichroic filter 318 may be positioned downstream of the one or more third optical components 310 to reflect light from the third illuminator module 306 toward the light output 314. The second dichroic filter 318 is configured to reflect light in the wavelength band(s) generated by the third illuminator 306 toward the output 314 and to pass light in the wavelength band(s) generated by the first illuminator module 302 and the second illuminator module 304. One or more optical elements 350 can be positioned downstream of the second dichroic filter 318 for focusing or otherwise controlling the combined light upstream of the output 314.

The illuminators of the illuminator modules 302, 304, 306 are each controlled by a controller 320. Controller 320 is configured to control the illuminators to generate illumination light for medical imaging according to multiple imaging modalities. The controller 320 may be configured to independently control illuminators generating different wavelength bands. For example, the controller 320 may be configured to independently control two illuminators of the same illuminator module that are configured to generate different wavelength bands. The controller 320 is configured to control the illuminator(s) of one illuminator module independently of the illuminator(s) of another illuminator module.

The controller 320 may be communicatively connected to one or more external systems via a communication port 322 for exchanging information regarding illumination between the illumination system 300 and the one or more external systems. In some examples, instructions for switching illumination modes are received via the communication port 322. For example, an imaging system controller may instruct the illumination system via communication port 322 to switch from a first illumination mode to a second illumination mode. Information for controlling illumination within a given mode may be received from the one or more external systems. For example, a brightness command and/or color balance command may be received at the controller 320 and the controller 320 may control one or more of the illuminators (via their respective drivers) to adjust the illumination output accordingly.

Figure 3B:
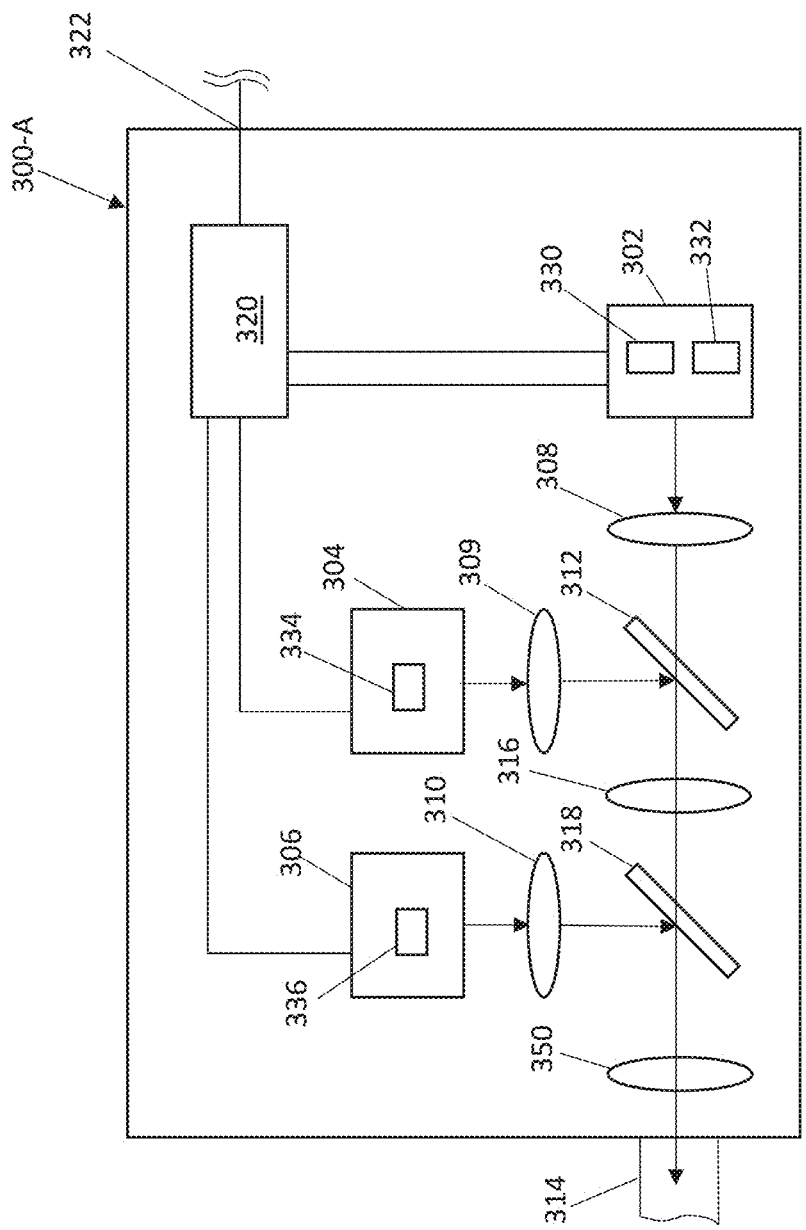
FIG. 3B illustrates a variation of the system of FIG. 3A that is configured for generating illumination light for white light and near-infrared imaging modalities.

FIG. 3B illustrates a variation of system 300 that is configured for generating illumination light for white light and near-infrared imaging modalities, according to some examples. Illumination system 300-A may include red, green, and blue light emitters for generating white light for white light imaging and one or more near-infrared light emitters for generating near-infrared fluorescence excitation light for near-infrared fluorescence imaging. The first illuminator module 302 may be configured as a dual-color illuminator module that provides the red light and the near-infrared light. The first illuminator module 302 may include one or more red light emitters 330 and one or more near-infrared light emitters 332 in a single light emitter package. For example, the first illuminator module 302 can be configured in similar fashion to the multi-color illuminator module 201 of FIG. 2 with the first light emitter 206 configured to emit red light and the second light emitter 208 configured to emit near-infrared light.

In some examples, the second illuminator module 304 can be configured as a single-color illuminator module that has one or more green light emitters 334. In some examples, the third illuminator module 306 can be configured as a single-color illuminator module that has one or more blue light emitters 336.

The first dichroic filter 312 can be configured as a long-pass filter to pass light having wavelengths in the red portion of the spectrum and longer wavelengths and reflect light having wavelengths shorter than the red portion of the spectrum. Thus, the red light and near-infrared light from the first illuminator module 302 passes through the first dichroic filter 312 and the green light from the second illuminator module 304 is reflected by the first dichroic filter 312.

The second dichroic filter 318 can be configured as a long-pass filter to pass light having wavelengths longer than the blue portion of the spectrum and reflect light having wavelengths in the blue portion of the spectrum and shorter wavelengths. Thus, the red light and near-infrared light from the first illuminator module 302 and the green light from the second illuminator module 304 passes through the second dichroic filter 318 and the blue light from the third illuminator module 306 is reflected by the second dichroic filter 318 toward the light output 314.

The controller 320 can be configured to control the emitters of the illumination system 300-A to operate in a first mode for generating white light for illuminating an imaging field of view. The controller 320 activates the red emitter(s) 330 of the first illuminator module 302, the green emitter(s) 334 of the second illuminator module 304, and the blue emitter(s) 336 of the third illuminator module 306, the light of which combines to produce white light. The near-infrared light emitter(s) 332 may be deactivated during the first mode. In some examples, the controller 320 can adjust the relative intensities of the emitters 330, 334, 336 to adjust the color temperature of the white light. The near-infrared light emitter(s) 332 may remain deactivated during the first mode.

The controller 320 can be configured to control the emitters of the illumination system 300-A to operate in a second mode for illuminating an imaging field of view with fluorescence excitation light for fluorescence imaging. The controller 320 activates the near-infrared light emitter(s) 332 and deactivates the red emitter(s) 330 of the first illuminator module 302. In some examples, the green emitter(s) 334 of the second illuminator module 304 and the blue emitter(s) 336 of the third illuminator module 306 are also deactivated along with the red light emitter(s) 330 of the first illuminator module 302. In other examples, one or more of the blue light emitter(s) 336 and the green light emitter(s) 334 remain activated while the near-infrared light emitter(s) 332 is activated. In some examples, the controller 320 is configured to maintain the illumination system 300-A in the first mode and/or the second mode for a continuous period, such as for a plurality of imaging frames. In some examples, the controller 320 is configured to switch between the first and second mode in a periodic manner such as to support combined white light and fluorescence imaging. For example, the controller may rapidly alternate activation of the red light emitter(s) 330 and the near-infrared light emitter(s) 332, such as at an imaging system imager frame rate. The imaging system may capture a white light frame when the red light emitter(s) 330 are activated (along with the green and blue light emitter(s) 334, 336) and may capture a fluorescence frame when the red light emitter(s) 330 are deactivated and the near-infrared light emitter(s) 332 are activated.

In some examples, the controller 320 can switch between the two illumination modes in response to a command from an imaging system, such as via communication port 322, and/or through a user interface of the illumination system 300-A. In some examples, the controller 320 switches between the two illumination modes based on a pre-determined switching regime, such as to support combined white light and fluorescence imaging. In some examples, a timing signal for the pre-determined switching regime is received from the imaging system via the communication port 322.

Figure 3C:
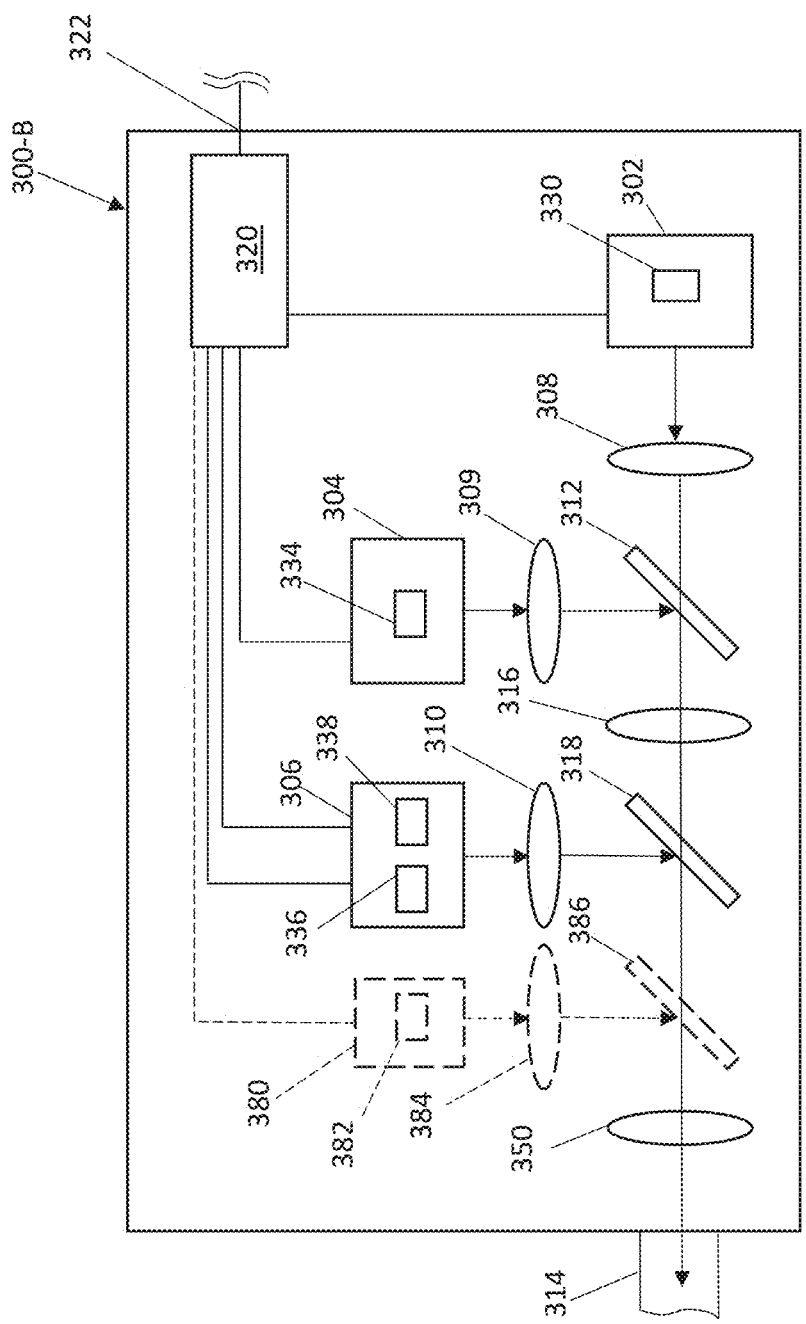
FIG. 3C illustrates a variation of the system of FIG. 3A that is configured for generating illumination light for white light and narrow band imaging modalities.

FIG. 3C illustrates a variation of system 300 that is configured for generating illumination light for white light and narrow band imaging modalities, according to some examples. Illumination system 300-B may include red, green, and blue light emitters for generating white light for white light imaging and one or more ultraviolet light emitters that can be used for fluorescence excitation (e.g., for exciting protoporphyrin IX fluorescence) and/or for narrow-band imaging. In some examples, the third illuminator module 306 may be configured as a dual-color illuminator module that provides the blue light and the ultraviolet light. The third illuminator module 306 may include one or more blue light emitters 336 and one or more ultraviolet light emitters 338 in a single light emitter package. For example, the third illuminator module 306 can be configured in similar fashion to the multi-color illuminator module 201 of FIG. 2 with the first light emitter 206 configured to emit blue light and the second light emitter 208 configured to emit ultraviolet light.

In some examples, the second illuminator module 304 can be configured as a single-color illuminator module that has one or more green light emitters 334. In some examples, the first illuminator module 302 can be configured as a single-color illuminator module that has one or more red light emitters 330.

The first and second dichroic filters 312, 318 can be configured the same as in system 300-A, since the ultraviolet light from the ultraviolet light emitter(s) 338 has wavelengths below that of blue light, the ultraviolet light will be reflected by the second dichroic filter 318 along with the blue light.

The controller 320 can be configured to control the emitters of the illumination system 300-B to operate in a first mode for generating white light for illuminating an imaging field of view. The controller 320 activates the red emitter(s) 330 of the first illuminator module 302, the green emitter(s) 334 of the second illuminator module 304, and the blue emitter(s) 336 of the third illuminator module 306, the light of which combines to produce white light. The ultraviolet light emitter(s) 338 may remain deactivated during the first mode.

The controller 320 can be configured to control the emitters of the illumination system 300-B to operate in a second mode for illuminating an imaging field of view with ultraviolet light and green light for narrow-band imaging. The controller 320 activates the ultraviolet light emitter(s) 338 and deactivates the blue light emitter(s) 336 of the third illuminator module 306. The green light emitter(s) 334 of the second illuminator module 304 remain activated. In some examples, the red light emitter(s) 330 of the first illuminator module 302 are deactivated. In some examples, the controller 320 is configured to maintain the illumination system 300-A in the first mode and/or the second mode for a continuous period, such as for a plurality of imaging frames. In some examples, the controller 320 can switch between the two illumination modes in response to a command from an imaging system, such as via communication port 322, and/or through a user interface of the illumination system 300-B.

In some examples, the illumination system 300-B includes a fourth illuminator module 380 that may include an emitter 382 for generating near-infrared fluorescence excitation light. The emitter 382 can include, for example, a laser diode or an LED. Light from the emitter 382 may be shaped by one or more optical components 384 and may be redirected toward the outlet 314 by a dichroic filter 386, which may be configured to pass near-infrared wavelengths and pass wavelengths below near-infrared wavelengths. The controller 320 can be configured to control the illuminator module 380 to provide near-infrared fluorescence excitation, such as in a third mode.

Figure 3D:
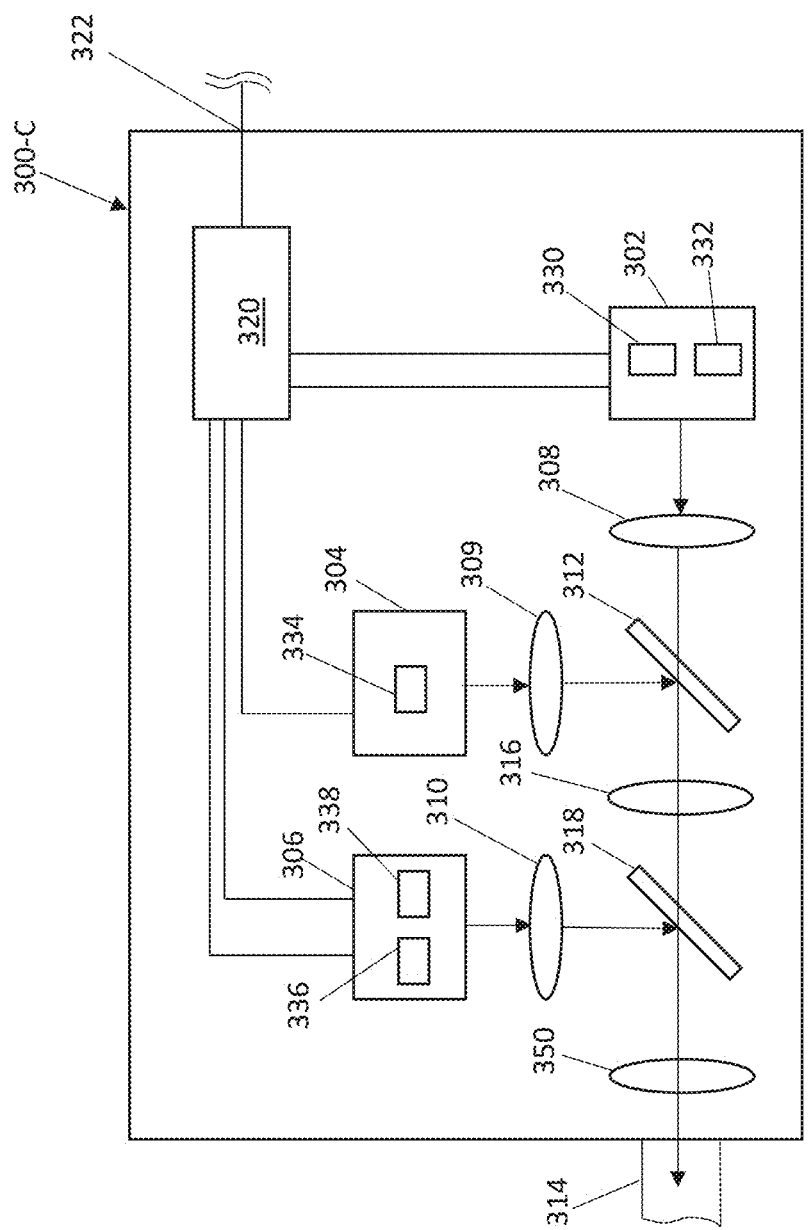
FIG. 3D illustrates a variation of the system of FIG. 3A that is configured for providing five colors with just three illuminator modules.

FIG. 3D illustrates a variation of system 300 that is configured for providing five colors with just three illuminator modules. Illumination system 300-C combines aspects of illumination systems 300-A and 300-B and red, green, and blue light emitters for generating white light for white light imaging, one or more ultraviolet light emitters for fluorescence excitation and/or for narrow-band imaging, and one or more near-infrared light emitters for generating near-infrared fluorescence excitation light for fluorescence imaging. The first illuminator module 302 and the third illuminator module 306 may each be configured as a dual-color illuminator module. The first illuminator module 302 may include one or more red light emitters 330 and one or more near-infrared light emitters 332 in a single light emitter package. The third illuminator module 306 may include one or more blue light emitters 336 and one or more ultraviolet light emitters 338 in a single light emitter package. The second illuminator module 304 may be a single-color illuminator module that includes one or more green light emitters 334. The controller 320 may be configured to control the emitters 330, 332, 334, 336, 338 to provide at least three different illumination modes—white light, fluorescence excitation light for fluorescence imaging, and combined green and ultraviolet light for narrow-band imaging—in similar fashion to the respective control of systems 300-A and 300-B discussed above.

The various illumination system configurations described above are merely exemplary. Any number of colors can be combined into the same channel and any number of multi-color channels can be combined with any number of single-color channels. According to some examples, a single channel can include all colors of the light source. For example, a light source configured to provide white light, ultraviolet light, and near-infrared red light can include a single channel that includes at least one red emitter, at least one green emitter, at least one blue emitter, at least one ultraviolet emitter, and at least one near-infrared emitter. According to some examples, a light source configured to provide white light, ultraviolet light, and near-infrared red light can include a dual color channel can include red and near-infrared emitters and a triple color channel can include green, blue, and ultraviolet emitters. According to some examples, a light source configured to provide white light, ultraviolet light, and near-infrared red light can include a triple-color channel that includes red, green, and blue emitters, a first single color channel that includes a near-infrared emitter, and a second single color channel that includes an ultraviolet emitter. In some examples, a light source may include a single channel that has one or more white light emitters and a one or more non-visible emitters, such as one or more infrared emitters and/or one or more ultraviolet emitters.

Figure 4:
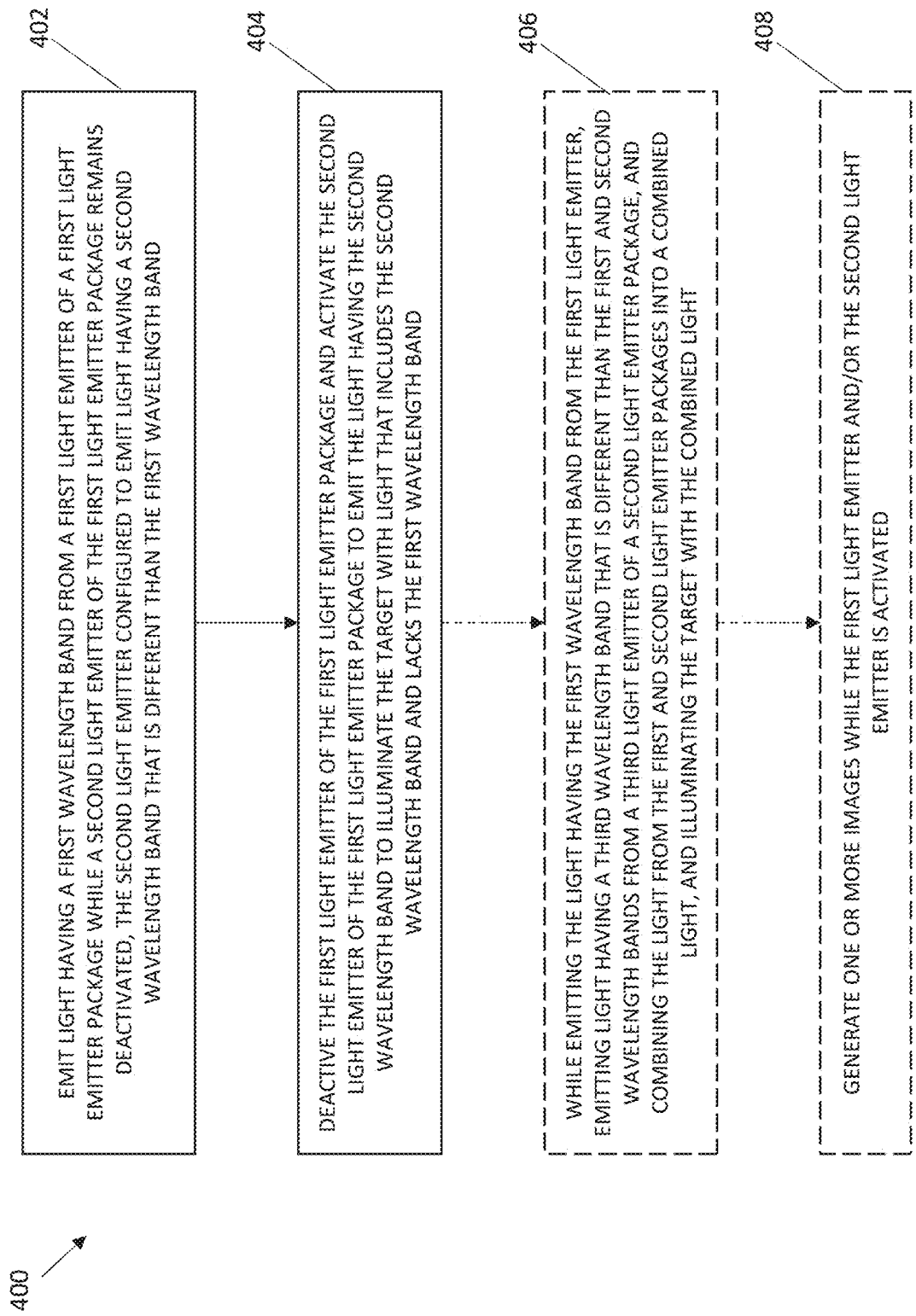
FIG. 4 is a block diagram of an exemplary method for illuminating a target for medical imaging.

FIG. 4 is a block diagram of a method 400 for illuminating a target for medical imaging, according to various examples. Method 400 can be performed by an illumination system in which at least two different light wavelength bands are provided by at least two different light emitters of the same light emitter package, such as illumination system 200 of FIG. 2, illumination system 300 of FIG. 3A, illumination system 300-A of FIG. 3B, illumination system 300-B of FIG. 3C, and illumination system 300-C of FIG. 3D. In some examples, a controller of an illumination system may include a processor configured to execute instructions stored in memory for performing one or more steps of method 400.

Method 400 can be performed during a medical imaging procedure for providing illumination light to support one or more imaging modalities. It is noted that the method concerns the operating of the light source. There is no functional link between the method and effects produced by the light source on the body. In some examples, the one or more imaging modalities can include white light imaging in which the illumination system provides white light, fluorescence imaging in which the illumination system provides fluorescence excitation light, such as infrared light and/or ultraviolet light, narrow-band imaging in which the illumination system provides ultraviolet light and green light, and/or combinations thereof. In some examples, the medical imaging procedure is a surgical procedure, such as a minimally invasive surgical procedure. In some examples, the medical imaging procedure is a non-invasive procedure. Illumination light generated according to method 400 can be provided to an imaging system or component thereof, such as to an endoscopic imager or a handheld imager via a light cable. The endoscope can be pre-inserted into the body. The method can exclude the step of inserting the endoscope into the body.

At step 402, light having a first wavelength band is emitted from a first light emitter of a first light emitter package while a second light emitter of the first light emitter package remains deactivated. The second light emitter is configured to emit light having a second wavelength band that is different than the first wavelength band. For example, with reference to system 200 of FIG. 2, the first light emitter 206 may be a red LED and the second light emitter 208 may be a near-infrared fluorescence excitation LED and the red LED may be activated while the near-infrared fluorescence excitation LED is deactivated.

At step 404, the first light emitter is deactivated and the second light emitter is activated and emits light having the second wavelength band to illuminate the target with light that includes the second wavelength band and lacks the first wavelength band. For example, the red LED may be deactivated and the near-infrared fluorescence excitation LED may be activated.

According to some examples, method 400 may further include optional step 406 in which light having a third wavelength band that is different than the first and second wavelength bands is emitted from a light emitter of a second light emitter package of the illumination system. The light from the light emitter of the second light emitter package is emitted while the light having the first wavelength band is emitted from the first light emitter of the first light emitter package—i.e., the light having the first wavelength band and the light having the third wavelength band are emitted simultaneously. The light from the light emitter of the second light emitter package combines with the light from the first light emitter of the first light emitter package, such as via one or more optical components, and the combined light is provided to the target for illuminating the target with light that includes the first and third wavelength bands. For example, with reference to system 300-A of FIG. 3B, the red light emitter 330 and the green light emitter 334 may be activated at the same time while the near-infrared light emitter 332 is deactivated. The blue light emitter 336 may also be activated to provide white light to the target. In some examples, the red light emitter 330 is then deactivated and the near-infrared light emitter 332 is activated. In some examples, the green and blue light emitters 334, 336 are deactivated when the red light emitter 330 is deactivated and in other examples, the green and blue light emitters 334, 336 remain activated.

Method 400 may include optional step 408 in which one or more images (single image or video frames) are generated via an imaging system of the target while light from the first light emitter is illuminating the target and/or while light from the second light emitter is illuminating the target. The imaging system includes an imager, which can be, for example, an endoscopic imager or an open-field imager. The imaging system may control the illumination system for switching between providing the first bandwidth light and providing the second bandwidth light.

In some examples, a first temporal sequence of images (e.g., video frames) may be generated while the first light emitter is activated and the second light emitter is deactivated and a second temporal sequence of images may be generated while the second light emitter is activated and the first light emitter is deactivated. According to some examples, a temporal sequence of images may be generated while the first and second light emitters are alternatingly activated/deactivated according to a timing scheme such that a first image is captured while the first emitter is activated and the second emitter is deactivated and a succeeding image is captured while the first emitter is deactivated and the second emitter is activated.

In some examples, method 400 can include switching between three different illumination modes to support three different imaging modalities. A first mode can be a white light mode in which the first emitter is a red light emitter, the third light emitter is a green light, and a fourth light emitter is a blue light, and the first, third, and fourth light emitters are activated at the same time to provide white light. A second mode can be a fluorescence excitation mode in which the second emitter is configured to generate fluorescence excitation light and is activated while the red light emitter is deactivated. A third mode can be a narrow-band imaging mode in which an ultraviolet light emitter that is part of the same light emitter package as the fourth light emitter (the blue light emitter) is activated at the same time as the green light emitter while the blue light emitter remains deactivated. In some examples, the illumination system can switch between these three modes as needed to support the three imaging modalities.

For the purpose of clarity and a concise description, features are described herein as part of the same or separate examples; however, it will be appreciated that the scope of the disclosure includes examples having combinations of all or some of the features described.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A light source for illuminating a target for medical imaging, the light source comprising:
    a first light emitter package comprising a first light emitter that emits light having a first wavelength band and a second light emitter that emits light having a second wavelength band that is different than the first wavelength band;
    a first heat sink for dissipating heat from the first light emitter package; and
    a controller for operating the light source in a first mode in which the first light emitter is activated and the second light emitter is deactivated and a second mode in which the first light emitter is deactivated and the second light emitter is activated, wherein the first light emitter generates a first amount of heat when activated in the first mode, the second light emitter generates a second amount of heat when activated in the second mode, and a sum of the first amount of heat and the second amount of heat is greater than a heat dissipation capacity of the first heat sink.

2. The light source of claim 1, further comprising:
    a second light emitter package comprising a third light emitter that emits light having a third wavelength band that is different than the first and second wavelength bands; and
    a first optical element for combining emissions from at least the first and second light emitter packages into a combined light beam,
    wherein the controller is configured so that, in the first light mode, the third light emitter is activated.

3. The light source of claim 2, wherein the first light emitter package comprises a substrate and the first light emitter and the second light emitter are mounted directly to the substrate.

4. The light source of claim 2, comprising a second heat sink for dissipating heat from the second light emitter package.

5. The light source of claim 2, comprising a second optical element located in front of the first light emitter and the second light emitter for receiving light from the first light emitter and the second light emitter and directing the received light to the first optical element.

6. The light source of claim 2, wherein the third light emitter is activated in the second mode.

7. The light source of claim 2, wherein the light having the first wavelength band and the light having the third wavelength band include visible light and the light having the second wavelength band includes non-visible light.

8. The light source of claim 7, wherein the non-visible light comprises ultraviolet light.

9. The light source of claim 7, wherein the non-visible light comprises infrared light.

10. The light source of claim 2, further comprising a third light emitter package comprising a fourth light emitter that emits light having a fourth wavelength band that is different than the first, second, and third wavelength bands, and wherein the controller activates the fourth light emitter along with the first light emitter and the third light emitter in the first mode for generating white light.

11. The light source of claim 2, wherein the controller is configured to control the first light emitter and the second light emitter so that the first light emitter and the second light emitter are not activated at the same time.

12. The light source of claim 2, wherein the first light emitter package comprises a plurality of first light emitters and a plurality of second light emitters.

13. The light source of claim 12, wherein the first light emitters are mosaiced with the second light emitters.

14. The light source of claim 2, wherein the light source is configured for endoscopic imaging.

15. A method for illuminating a target for medical imaging, the method comprising:
   emitting light having a first wavelength band from a first light emitter of a first light emitter package while a second light emitter of the first light emitter package remains deactivated, wherein emitting the light from the first light emitter generates a first amount of heat, and wherein the second light emitter is configured to emit light having a second wavelength band that is different than the first wavelength band; and
   deactivating the first light emitter of the first light emitter package and activating the second light emitter of the first light emitter package to emit the light having the second wavelength band to illuminate the target with light that includes the second wavelength band and lacks the first wavelength band, wherein emitting the light from the second light emitter generates a second amount of heat, and wherein a sum of the first amount of heat and the second amount of heat is greater than a heat dissipation capacity of a first heat sink for dissipating heat from the first light emitter package.

16. The method of claim 15, further comprising, while emitting the light having the first wavelength band from the first light emitter, emitting light having a third wavelength band that is different than the first and second wavelength bands from a third light emitter of a second light emitter package, and combining the light from the first and second light emitter packages into a combined light, and illuminating the target with the combined light.

17. The method of claim 16, further comprising while emitting the light having the first wavelength band and the light having the third wavelength band, generating a temporal sequence of images of the target.

18. The method of claim 16, further comprising while emitting the light having the first and third wavelength bands, emitting light having a fourth wavelength band that is different from the first and third wavelength bands to generate white light.

19. The method of claim 16, wherein a second heat sink that is different than the first heat sink dissipates heat from the second light emitter package.

20. The method of claim 16, wherein the third light emitter remains activated while the first light emitter is deactivated and the second light emitter is activated.

21. The method of claim 16, wherein the light having the first wavelength band and the light having the third wavelength band include visible light and the light having the second wavelength band includes non-visible light.

22. The method of claim 21, wherein the non-visible light comprises ultraviolet light.

23. The method of claim 21, wherein the non-visible light comprises infrared light.

24. The method of claim 15, further comprising generating a temporal sequence of images while alternatingly activating and deactivating the first and second light emitters.

25. The method of claim 15, wherein the first light emitter package comprises a substrate and the first light emitter and the second light emitter are mounted directly to the substrate.

26. The method of claim 15, comprising illuminating the target with an endoscope.

* * * * *